United States Patent
Sanyal

Patent Number: 6,126,616
Date of Patent: Oct. 3, 2000

[54] COLLECTION OF BIOLOGICAL PRODUCTS FROM HUMAN ACCESSORY REPRODUCTIVE ORGANS BY ABSORBENT SYSTEMS

[76] Inventor: Mrinal K. Sanyal, 30 Village Pond Rd., Guilford, Conn. 06437

[21] Appl. No.: 09/337,599

[22] Filed: Jun. 21, 1999

[51] Int. Cl.[7] ............................. A61B 10/00; A61F 5/44
[52] U.S. Cl. .................... 600/562; 600/573; 604/330; 128/834; 128/837; 128/841
[58] Field of Search ..................... 600/562, 572, 600/573, 574, 830; 128/832, 834, 837, 841; 604/317, 327, 328, 330, 337, 338, 347, 354, 358

[56] References Cited

U.S. PATENT DOCUMENTS

| | | | |
|---|---|---|---|
| 3,128,767 | 4/1964 | Nolan | 604/330 |
| 3,216,422 | 11/1965 | Steiger et al. | 604/330 |
| 3,636,940 | 1/1972 | Gravlee | 128/2 |
| 3,948,270 | 4/1976 | Hanson | 128/348 |
| 3,983,874 | 10/1976 | Davis et al. | 604/330 |
| 4,142,476 | 3/1979 | Hirschman | 112/262 |
| 4,175,561 | 11/1979 | Hirschman | 128/270 |
| 4,196,562 | 4/1980 | Hirschman | 156/217 |
| 4,245,653 | 1/1981 | Weaver | 128/749 |
| 4,517,970 | 5/1985 | Goepp et al. | 128/841 |
| 5,044,376 | 9/1991 | Shields | 128/837 |
| 5,073,202 | 12/1991 | Wallach | 134/6 |
| 5,231,992 | 8/1993 | Leon | 600/572 |
| 5,415,994 | 5/1995 | Imrich et al. | 435/7.32 |
| 5,421,346 | 6/1995 | Sanyal | 128/760 |
| 5,571,540 | 11/1996 | Weyenberg et al. | 425/343 |
| 5,725,481 | 3/1998 | Buck et al. | 128/759 |
| 5,743,893 | 4/1998 | Kalb | 604/317 |
| 5,876,389 | 3/1999 | Bouchard et al. | 604/386.16 |
| 5,916,205 | 6/1999 | Olson et al. | 604/385.17 |
| 5,928,184 | 7/1999 | Etheredge et al. | 604/15 |

OTHER PUBLICATIONS

Article dated Nov. 1954; by George N. Papanicolaou, M.D.; Cytological Evaluation of Smears Prepared by the Tampon Method for the Detection of Carcinoma of the Uterine Cervix (6 pages).

Article dated Feb. 1, 1985; by Arnold Bernstein, M.D., Saul Vitner, M.D., and Joe M. Webber, M.D.; Evaluation of a New Tampon Device for Cytologic Autocollection and Mass Screening of Cervical Cancer and its Precursors (8 pages).

Article dated 1993; Advances in Gynecological and Obstetric Research Series; vol. 3; Chapt. 42; by H. Pickel; Adenocarcinoma in Situ of the Uterine Cervix (5 pages).

Article dated Jan. 1996; Am J Obsts Gynecol; vol. 174; No. 1; Part 1; by Geraldine Blanch, Karl S.J. Olah, and Steve Walkinshaw; The Presence of Fetal Fibronectin in the Cervicovaginal Secretions of Women at Term—Its Role in the Assessment of Women Before Labor Induction and in the Investigation of the Physiologic Mechanisms of Labor (5 pages).

Article dated 1995; Prostaglandins 50: 179–188; by Hans Bokstrom and Nils Wiqvist; Prosaglandin Release From Human Cervical Tissue in the First Trimester of Pregnancy After Preoperative Dilatation With Hygroscopic Tents (10 pages).

*Primary Examiner*—Cary O'Connor
*Assistant Examiner*—Charles Marmor, II
*Attorney, Agent, or Firm*—Browning Bushman

[57] ABSTRACT

A cervical collection device (20) for collecting uterine and cervical secretions for medical diagnostic purposes. The cervical collection device (20) is placed over the cervical opening (14). Collection device (20) includes an outer elastomeric receptacle (22) of a hemispherical shape having a collection capsule or pad (26) fitting thereon. Collection pad (26) includes an inner layer or core (28) of absorbent material and an outer water-resistant cover (32). Collection member (26) has an outer convex surface conforming to the inner surface of the elastomeric receptacle (22). Receptacle (22) has an outer rim (24) arranged for fitting over the cervical opening (14) for removable securement of collection device (20) to a user. Inner layer (28) may be formed of various materials and impregnated with selected substances.

15 Claims, 1 Drawing Sheet

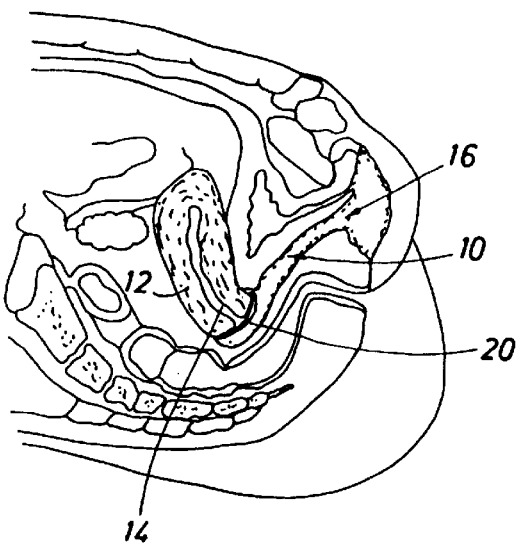
FIG.1
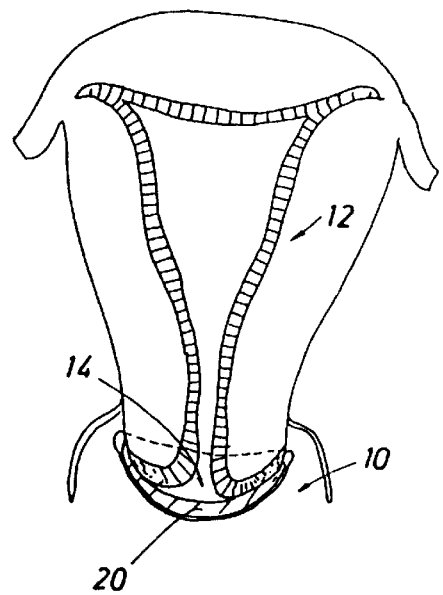
FIG.2
FIG.3
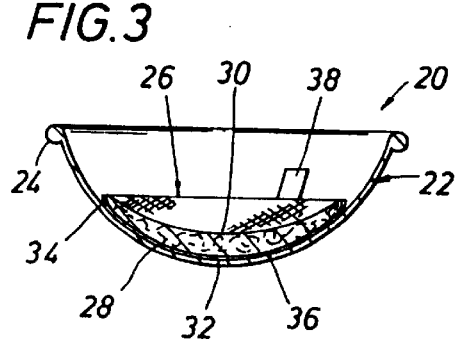
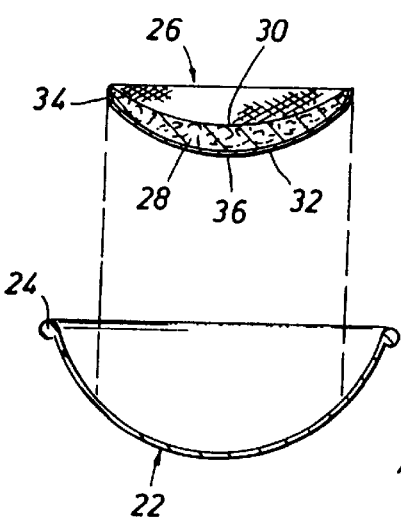
FIG.4
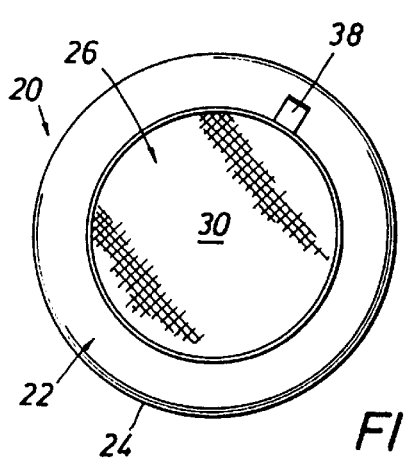
FIG.5

COLLECTION OF BIOLOGICAL PRODUCTS FROM HUMAN ACCESSORY REPRODUCTIVE ORGANS BY ABSORBENT SYSTEMS

FIELD OF THE INVENTION

The present invention relates to devices and procedures for recovery of cells, secretions, discharges and products of conception from human female accessory reproductive organs. These devices are safe, nontraumatic and can be routinely used for assessment of reproductive status, optimization of reproductive outcome and diagnosis of disease and disorder of such organs.

BACKGROUND OF THE INVENTION

The fallopian tubes, uterus, cervix, vagina and external genitalia are female accessory reproductive organs essential for human procreation. These organs exhibit cyclic cellular changes, and their secretory capability is induced by numerous endocrine, paracrine, and autocrine factors that are generated by the same tissues or other organs of the body. The accessory reproductive organs provide support for fertilization and early embryonic differentiation, allow pregnancy maintenance and fetal development, and finally, parturition and birth of the baby. Numerous studies have shown that various processes of early embryonic development, differentiation of the conceptus (fetus and placenta) and pregnancy conditions can be established by cellular and molecular markers in products derived from such organs. In addition, numerous diseases of accessory reproductive organs related to infertility, neoplasia, and infections can also be detected in secreted fluids, discharges and exfoliated cells of these organs.

Therefore, new devices and procedures have been developed for: (i) collection of human uterine and cervical cells and secretions produced naturally or that resulted from treatment with drugs and therapeutic procedures; (ii) collection of live cells from uterus and cervix and microbes to allow their in vitro culture, and preservation of macromolecules and biochemical components of such cells and secretions suitable for diagnostic tests by cellular and molecular methods; and (iii) collection of menstrual discharges and conception products of spontaneous abortions and premature births for diagnosis of metabolic diseases of the mother or disorders of conception. These devices are designed for self collection of biological products available for diagnosis of cancer and infertility diseases, assessment of microbial infections, and pregnancy statuses by cellular, biochemical and molecular analyses.

It is known that alumina particles or gels derived from aluminum oxides and hydroxides have absorption and desiccation properties. Another silica product useful in this regard is hydrogel. It allows efficient absorption of liquid because of its porous nature. In addition, bioploymers [e.g., (polyethylene glycol)] have been developed for protection and delivery of biologically active short-lived molecules. Utilizing such materials and others, effluent collection systems of capsules and pads, and supportive structures, for the human uterus and cervix, have been developed.

U.S. Pat. No. 5,725,481 dated Mar. 10, 1998 is directed to a method and apparatus for collecting vaginal fluid and vaginal cells including an absorbent device inserted within the vagina. The absorbent device includes a core having a highly absorbent material and an outer covering made of a porous material to permit fluid to pass into the inner core. The vaginal device described is distinctly different from this device with capsules of absorbent materials containing compounds for enhancing the subsequent diagnostic testing.

SUMMARY OF THE INVENTION

The present invention has been designed to collect biological materials from the human uterus and cervix by absorbent capsules or pads of: (a) compressed natural cotton or synthetic fiber mesh, (b) synthetic sponge, (c) or hydrogel. These absorption bases may be impregnated with alumina particles or gel for absorption of water and/or polyethylene glycol for preservation of cell viability and biological activity of macromolecules. In addition such absorption bases may contain tissue culture media and medication for prevention of microbial growth.

The support device for holding the absorbent pad or capsule for collection of biological materials derived from human uterus and cervix preferably comprises a cervical cup to be placed over the cervix.

The surface of the absorbent substrate next to the human cervical tissue is separated by highly porous membranes of synthetic polymer materials and/or meshes of cotton fibers of low or no immunosensitivity. The pads or capsules preferably contain tissue culture media with antibiotics to prevent microbial survival and growth, or have organic and inorganic agents for preserving cells and biological molecules.

Other features and advantages of the invention will be apparent from the specification and drawings.

BRIEF DESCRIPTION OF THE DRAWINGS

FIG. 1 shows diagrammatically in cross section the feminine anatomy in the urethral area with a cervical device of the invention fitted over the cervix;

FIG. 2 is a diagrammatic view of only the uterus and cervix with the invention fitted over the cervix;

FIG. 3 is a cross sectional view of the cervical device shown in FIGS. 1 and 2 removed from the body of a user and comprising an outer flexible cup having a removable collection pad mounted therein;

FIG. 4 is an exploded view of the cervical device shown in FIG. 3 with the collection pad removed from the outer cup; and FIG. 5 is a top plan of the cervical device shown in FIGS. 1–4.

DESCRIPTION OF THE INVENTION

Referring in particular to FIGS. 1 and 2, the female anatomy is shown diagrammatically including a vagina 10 and a uterus generally indicated at 12 having a cervical opening 14. Vagina 10 and vulva 16 are defined by labia.

A cervical device generally indicated at 20 is shown further in FIGS. 3–5 of the present invention and is adapted for fitting over the utero-cervical opening 14. Cervical device 20 has an outer cup-shaped receptacle 22 preferably formed of an elastomeric material such as a polymer latex material. Receptacle 22 is of a hemispherical shape and has an outer rim 24 extending about the open end of receptacle 22 for fitting about the cervical protrusion within the vaginal tube at utero-cervical opening 14. Receptacle 22 is positioned over opening 14.

Fitting within receptacle 22 is an effluent collection capsule or pad 26 as shown particularly in FIGS. 3 and 4. Pad 26 is formed of a highly porous inner layer 28 defining an inner concave surface 30 and an outer layer 32 of a water resistant material defining a convex surface 36. A marginal side portion 34 of layer 32 extends along the outer periphery of inner layer 28. Outer waterproof or water resistant layer 32 is formed of a paper or plastic material. An adhesive material is provided on convex surface 36 for releasably securing effluent collection pad 26 within outer cup-shaped receptacle 22. Outer layer 32 has a pull tab 38 to permit pad 26 to be easily removed from receptacle 22. Rim 24 is sufficiently flexible to fit the protruding cervix within the vaginal tube for covering opening 14. The diameter of rim 24 is about two (2) inches and rim 24 may be easily distended to fit the cervix firmly. The size of receptacle 22 may vary for different users.

Pad 26 is of a generally bowl-shaped or cup-shaped configuration in cross section and the pad 26 has a maximum thickness of about ¼ inch at its center. Pad 26 is progressively attenuated from its center toward its periphery which is covered by marginal side portion 34 of the lower water-resistant layer 32. Tab 38 may comprise a thin plastic tab which is embedded within pad 26. Concave surface 30 of layer 28 includes a thin, highly porous cotton or biopolymer membrane of about 1/32 inch to 1/16 inch in thickness to provide a highly reduced or negative immune reaction. The highly porous concave surface 30 allows initial filteration of cells and secretions derived primarily from cervical and uterine tissues and produce no or highly reduced immune reaction.

Inner layer or core 28 is preferably selected from the following substrate substances: (a) compressed natural cotton or mesh of synthetic fiber; (b) synthetic sponge; (c) hydrogel and (d) alumina particle/gel with or without any additive. These substances may be moistened with a defined tissue culture medium (e.g., Medium 199) containing antibiotics (e.g., penicillin and streptomycin) preventing microorganism growth. The substrates of (a), (b) and (c) may also be impregnated with (d) alumina.

Use and Operation

The cervical cup device 20 is sterile and made of disposable materials primarily for one medical use by the human subject or the nurse or the physician. Transfer of these biological materials for laboratory analysis will be made in plastic enclosed containers. This device is to be used for the following diseases or disorders:

Cancer Screening: The cervical cup device 20 comprising the present invention is noninvasive and can be readily applied for self collection of biological material (exfoliated cells, secretory fluids, menstrual discharges) from the uterus and cervix of human subjects. Numerous cellular, genetic and chromosomal markers have now been identified for uterine and cervical cancers. The exfoliated cells and secretory products from cervix and uterine endometrial tissues preserved by tissue culture medium or biopolymer polyethylene glycol, allow establishing the possibility of disease.

Since diagnostic genetic tests, in particular those with nucleic acid, are now possible even with samples of dried blood or dislodged tissues in cotton and other substrates, menstrual discharges containing preneoplastic/neoplastic cells or exfoliated cells collected in capsules can be used for cancer diagnosis by such tests. The exfoliated neoplastic cells available in the sponge or hydrogel containing tissue culture fluid and antibiotics, maintained at body temperature, may be used for cytopathological analysis and molecular tests of oncogenic mutations or other macromolecular cancer markers. Such molecular and cellular tests in these biological materials permit screening for cancer of such organs. Positive initial tests for cancer using such materials could be an indication for additional in-depth screening by microarray or other advanced analytical systems.

Infertility/Pregnancy Disorders: The human female accessory reproductive tissues normally secrete fluids containing numerous macromolecular proteins reflecting the reproductive status, embryo implantation window, and infertility disorders due to aberrant growth of such tissues. Secretions of these tissues have been used in the past for ferning tests showing different composition of the secretion during different reproductive phases. Extension of such diagnostic fertility tests with molecular markers will be possible by the biological products accumulated in collection systems.

It is known that numerous pregnancies are lost due to a variety of biological causes in parents or in the conception itself. These devices allow collection of expelled conception products of natural spontaneous abortions or premature births for research and prevention of future pregnancy loss. A number of parameters for monitoring of labor and delivery (parturition) can also be assessed in such materials. Thus, detailed genetic and biochemical analyses of these materials in collection pads of the device may help prevention, diagnosis and therapy of various infertility and pregnancy disorders.

Microbiological Infection: The human accessory reproductive organs are a source of numerous disease producing microbes. Infections of yeast microploasma, chlamydia, gonorrhea and other sexually transmitted diseases are common in these organs. In addition, viral infections of cytomegalovirus, papilloma, and human immunodeficiency syndrome are also detected in these tissues. Infection with such microbial agents can be established and diagnosed by both culture, serological and molecular tests with such materials.

Advantage and Specific Application of the Method

Self collection systems for cervical sample collection have been attempted before by tampon devices. The procedure has remained unpopular because of various reasons related to sample collection. The cervical cup device is efficient as it is placed over the cervix and uterine ostium. It is in direct contact with the cervix and collects cervical cells and secretions. In addition, dislodged cells and secretions from the uterus may also accumulate in the capsule released through the cervical opening. Biological materials gathered are free from contamination of vaginal materials. Since the absorption components of the collection devices favor cell survival, specific cytological preparation for identification of diseases of the cervix and uterus is possible.

The cervical cup device of the present invention has numerous applications in gynecological and obstetrical practices. Some of these applications are listed below:

i. Routine monitoring of cancer of the uterus and cervix. This will be a major application of the cervical device. The cervical cell and secretion samples can be collected by the subject without a visit to the clinic and they can be sent for laboratory analysis. The device may collect uterine cells and secretions and materials of break through bleeding which may contain exfoliated uterine cancer cells; thereby providing samples for diagnosing endometrial and other uterine cancers.

ii. Diagnosis of infertility disorders. Availability of cells and secretions generated during diseased statuses of the uterus which can not support pregnancy initiation may allow identification of the infertility status. The biological materials collected by the cervical device may be analyzed for different parameters to predict the deficiency and suggest therapy of the infertility disorder.

iii. Early pregnancy detection. Analysis of cells and secretions collected by cervical device may predict the pregnancy at an early stage as the pregnancy parameters are directly available from the implanting conceptuses to that using blood or saliva of the subject in which the product parameters are filtrated by body mechanisms.

iv. Identification of embryo implantation window. Information on specific parameters in cells and secretions collected by the cervical cup and capsule will allow determination of the exact timing for embryo transfer into maternal uterus during in vitro fertilization procedure. Implantation window is short and identification of this period will improve pregnancy possibilities by this procedure.

v. Assessment of labor and deliver statuses. The cellular and secretory materials collected by the cervical device and the parameters measured will permit forecasting of the labor and delivery statuses. These parameters are expressed in cervical and uterine tissues during labor.

vi. Immunological incompatibility for implantation. The biological materials (cells, secretions, white blood cells, etc.) collected by the cervical device will allow assessment of immunological properties with respect to potential for implantation of the embryo and continuation of the pregnancy. Immunological compatibility can be readily determined in the cells and secretions collected by these devices by laboratory tests.

vii. Analysis of causes of spontaneous abortion. The collection of menstrual discharge, dislodged embryos or aborted fetuses expelled by the mother will be a major use of this system. At present, these materials are useful in diagnosing the specific causes of spontaneous abortions, early pregnancy wastage and menstrual disorders.

viii. Detection and diagnosis of microbial diseases. The cervical device can collect live materials, including bacteria, fungi, protozoans and viruses. Microbial samples collected can be cultured for cytological identification of the species or strain or tested biochemically and immunologically.

ix. In-depth analysis of cancer. Exfoliated live cells can be collected by the cervical device. Culture capability of live uterine and cervix cells collected is an important advantage since often cancer or other diseased cells in samples are few. Culture of live sample cells can increase the number of diseased cells, and facilitate detection of the disease using various cellular and biochemical laboratory tests.

x. Genome characteristics analysis. Biological material collected by these systems is a resource for in-depth DNA analysis for genetic mutation identifying the nature of the disease, risk or susceptibility for future disease by microarray or other advanced procedures.

While a preferred embodiment of the present invention has been illustrated in detail, it is apparent that modifications and adaptations of the preferred embodiment will occur to those skilled in the art. However, it is to be expressly understood that such modifications and adaptations are within the spirit and scope of the present invention as set forth in the following claims.

What is claimed is:

1. A cervical collection device for collecting cells and secretory products of human uterus and cervix comprising:

an outer bowl-shaped receptacle formed of an elastomeric material and being of a generally hemispherical shape having an open end; and a removable collection member removably fitting within said open end of said receptacle and having an outer surface conforming generally to the contour of the inner surface of said receptacle; said collection member having a relatively thin fluid impervious outer surface in contact with said inner surface of said receptacle and an adjacent fluid absorbent inner layer of a substantial thickness for collection of both uterine and of cervical secretions and exfoliated cells and tissues.

2. A cervical collection device as set forth in claim 1, wherein said bowl-shaped receptacle has an outer rim extending about and outwardly from said open end, said outer rim effecting securement of said collection device on a user.

3. A cervical collection device as set forth in claim 1 wherein a pull tab is secured to and extends from said collection member for effecting removal of said collection member from said receptacle.

4. A cervical collection device as set forth in claim 1, wherein said fluid impervious outer surface has adhesive thereon for removable securement of said collection member within said outer receptacle.

5. A cervical collection device as set forth in claim 1, wherein said fluid absorbent inner layer prepared with alumina material.

6. A cervical collection device as set forth in claim 1, wherein said fluid absorbent inner layer comprised of hydrogel.

7. A cervical collection device as set forth in claim 1, wherein said fluid absorbent inner layer comprised of a synthetic sponge material.

8. A cervical collection device as set forth in claim 1, wherein said fluid absorbent inner layer includes compressed cotton fibers.

9. A cervical collection device as set forth in claim 1, wherein said fluid absorbent inner layer includes cotton fibers impregnated with a tissue culture medium.

10. A cervical collection device as set forth in claim 1, wherein said inner layer comprises cotton impregnated with alumina material.

11. A cervical collection device as set forth in claim 1, wherein said inner layer is formed of hydrogel permeated with a tissue culture medium.

12. A cervical collection device as set forth in claim 1, wherein said inner layer is formed of synthetic sponge infused with a tissue culture medium.

13. A cervical collection device as set forth in claim 1, wherein said inner layers contains polyethylene glycol as a constituent in the tissue culture medium.

14. A cervical collection device for collecting cervical secretions comprising:

an outer bowl-shaped receptacle formed of an elastomeric material and having an outer rim arranged for securement of said receptacle over the cervix of a user; and a removable collection member removably fitting within said receptacle and having an outer shape conforming generally to the contour of the inner surface of said receptacle; said collection member having a relatively thin fluid impervious outer surface in contact with said inner surface of said receptacle and a fluid absorbent inner layer of a substantial thickness for collection of cervical secretions; said fluid impervious outer surface having a securing element thereon for removable securement of said collection member within said outer receptacle.

15. A cervical collection device as set forth in claim 14, wherein said fluid absorbent layer includes an absorbent material soaked with a tissue culture medium containing antibiotic medications for controlling microorganism growth.

* * * * *